United States Patent

Hahn

[11] Patent Number: 5,827,904
[45] Date of Patent: Oct. 27, 1998

[54] MEDICAL IMPLANT COMPOSITION

[76] Inventor: David Hahn, 7528 Oxford Cir., Dublin, Calif. 94568

[21] Appl. No.: 722,632

[22] Filed: Sep. 27, 1996

[51] Int. Cl.⁶ .............................. C08K 5/01; A61F 2/40; A61F 2/38
[52] U.S. Cl. ........................ 523/113; 524/483; 524/585; 623/19; 623/20; 514/763
[58] Field of Search ............................ 523/113; 524/585, 524/483; 252/398; 514/763; 623/19, 20

[56] References Cited

U.S. PATENT DOCUMENTS

| | | | |
|---|---|---|---|
| 3,932,546 | 1/1976 | Buchi et al. ............................ | 260/666 |
| 4,101,720 | 7/1978 | Taylor et al. ........................... | 523/126 |
| 4,121,025 | 10/1978 | Scott .......................................... | 526/4 |
| 4,127,455 | 11/1978 | Schulz et al. ............................ | 204/78 |
| 4,588,407 | 5/1986 | Isono et al. ................................ | 623/11 |
| 4,634,447 | 1/1987 | Isono et al. ................................ | 623/66 |
| 4,643,715 | 2/1987 | Isono et al. ................................ | 604/4 |
| 4,883,887 | 11/1989 | Bernhard et al. ....................... | 549/341 |
| 4,929,774 | 5/1990 | Fukamachi et al. .................... | 568/824 |
| 5,023,355 | 6/1991 | Globus et al. .......................... | 549/478 |
| 5,110,595 | 5/1992 | Wang ....................................... | 424/422 |
| 5,464,450 | 11/1995 | Buscemi et al. ............................ | 623/6 |
| 5,489,303 | 2/1996 | Sasaki et al. ............................ | 623/11 |
| 5,602,183 | 2/1997 | Martin et al. .......................... | 514/871 |

*Primary Examiner*—Andrew E. C. Merriam
*Attorney, Agent, or Firm*—Theodore J. Bielen, Jr.

[57] ABSTRACT

A composition for the manufacture of a medical implant utilizing a solid polymeric material fashioned from stock or pressure molded from a powder base. A sufficient amount of a carotenoid is doped into powder base or stock solid polymeric material to produce a stable oxidation resistant matrix for use in medical implants, or alternatively doped into a solid, performed bulk polymeric material for use as medical implants.

7 Claims, 10 Drawing Sheets

MEDICAL IMPLANT COMPOSITION

BACKGROUND OF THE INVENTION

The present invention relates to a novel and useful composition for the manufacture of medical implants.

Total joint replacement surgical procedures have now become commonplace in the medical field. In many instances, a polymeric material such as ultra-high molecular weight polyethylene, is used as the load bearing surface. Despite the apparent overall success of ultra-high molecular weight polyethylene as an implant material in total joint replacement operations, certain problems have arisen. For example, the ultra-high weight polyethylene tends to wear and create micron-sized and submicron-sized debris. Such wear typically takes place when the ultra-high molecular weight polyethylene contacts an opposing metal surface. In addition, a condition identified as osteolysis develops. In this condition, the natural bone begins to die and recede from the artificial joint. In such cases, revision surgery is necessary to correct this condition. It is believed that the submicron-sized wear debris has a role in creating osteolysis.

Certain preparations and mixtures have been proposed to stabilize oxidation sensitive compounds, such as vitamins. For example, U.S. Pat. No. 4,929,774 proposes a coating mixture for the same. U.S. Pat. No. 5,110,595 describes bio-absorbable implant preparations in the form of lipoidal fatty substances.

The degeneration of polymer compositions has been recognized, especially upon the exposure of such composition to light and heat. For example, U.S. Pat. No. 4,121,025 proposes a composition which controls the degree of degeneration of polymers.

U.S. Pat. Nos. 4,588,407; 4,634,447; 4,643,715; and 5,489,303 teach artificial organs that are implanted as artificial kidneys, livers, lungs, vessels, and the like. The artificial organs include a film of a fat soluble vitamin or a mixture of fat soluble vitamins with glycerin deposited on the surfaces of the parts. It is intended that secondary effects upon a living system are avoided by this expedient.

Carotenoids have been recognized as serving as an antioxidant capable of quenching singlet oxygen and scavenging free radical species. However, the behavior of beta carotene in the human body is very complex in that beta carotene and related compounds can participate in both anti-oxidant as well as pro-oxidative processes. This dual role is dependent on a number of parameters such as oxygen, partial pressures, and the like. U.S. Pat. Nos. 3,932,546; 4,127,455; 4,883,887; and 5,023,355 describe manufacturing techniques for carotenoids, such as beta carotene.

A composition for the manufacture of load bearing implants for the knee, shoulder, and the like would be a notable advance in the medical field.

SUMMARY OF THE INVENTION

In accordance with the present invention, a novel and useful composition for the manufacture for a load bearing medical implant is herein provided.

A polymeric solid material such as polyethylene, high density polyethylene, ultra-high molecular weight polyethylene, and the like serve as an excellent matrix for the material of the present invention. Simple solid polymeric material used alone is known in the prior art. The solid polymeric material may be formed into a mass, or into a powder or divided particles of a certain size.

The solid polymeric material may then be doped by the addition of a carotenoid such as beta carotene, xanthophyll, also known as lutein, and alpha carotene$^{-3-3-diol}$. Canthaxanthin, equinenone, cryptoflavin, and zeaxanthin may also serve this purpose. The carotenoid is doped into the solid polymeric material (either in powder or performed bulk form) through an organic solvent, such as an alcohol cyclohexane, and the like. Contact between the carotenoid and the solid polymeric material is continued over a period of time by soaking. The carotenoid doped into the stock polymeric material is believed to penetrate the surface of the solid material to a certain degree. The doped stock polymeric material may then be formed into a load bearing medical implant. The doped powder material may then be pressure molded or formed into a bulk load bearing solid material suitable for medical implants. It has been found that doping of the solid polymeric material by carotenoids decreases surface oxidation and the ester-carbonyl oxidation of the solid polymeric material. Such reduction in oxidation greatly reduces the wear of the solid polymeric material when implanted.

It may be apparent that a novel and useful composition for the manufacture of a medical implant has been described.

It is therefore an object of the present invention to provide a composition for the manufacture of a medical implant which may be easily formed or molded into specific implant components.

Another object of the present invention is to provide a composition for use as a medical implant which exhibits greatly reduced oxidation and exfoliation of micron-sized particles.

A further object of the present invention is to provide a composition useful as an implant material which helps prevent the development of osteolysis and the necessity of revision surgery.

The invention possesses other objects and advantages especially as concerns particular characteristics and features thereof which will be described hereinafter.

For a better understanding of the invention reference is made to the following detailed description of the preferred embodiments thereof which should be taken in conjunction with the hereinbefore described drawings.

DETAILED DESCRIPTION OF THE PREFERRED EMBODIMENTS

Various aspects of the present invention will evolve from the following detailed description of the preferred embodiments thereof which should be taken in conjunction with the prior described drawings.

The solid polymer material in the form of a ultra-high molecular weight polyethylene (UHMWPE) was synthesized in the form of a fine granular powder with nominal particle sizes at 150 microns. Bulk (UHMWPE) was also formed by direct molding of the powder at high pressure and temperature above the (UHMWPE) melting point (143 degrees centigrade).

Both the UHMWPE powder and bulk UHMWPE samples were doped with beta carotene by soaking the materials in solutions of beta carotene, isopropyl alcohol, and cyclohexane. Solutions strength ranged from 0.1 to 4.375 milligrams per milliliter of beta carotene-to-solvent. Soaking times were varied between 6–112 hours.

Raman spectroscopy was employed to verify the presence of beta-carotene utilizing fundamental of Raman bands at 1005, 1155, and 1514 $CM^{-1}$.

Since the doping of UHMWPE with beta carotene is primarily a diffusion controlled process. Any combination of a carotenoid such as beta carotene, xanthophyll, and the like with a suitable solvent, such as isopropyl alcohol (2-propanol), cyclohexane, n-hexane, benzene, and the like, may be employed in this invention. The doping levels of the carotenoid range from trace amounts to as much as 5%. A variation of the doping levels may be realized by a combination of soaking time, temperature, and solution strength. Depth profiling and mechanical testing were performed to assess the uniformity and utility of the beta carotene-doped UHWPE. In addition, samples were tested for effect on ester-carbonyl oxidation. Raman spectroscopy, in conjunction with depth profiling and cross-sectioning confirmed the ability to prepare homogeneously doped samples from beta carotene doped UHMWPE powder. In addition, penetration of the beta carotene doping of stock through the surface on the order of 150 milimicrons was confirmed. Reduction in oxidation of the beta carotene doped UHMWPE was also determined using FTIR spectroscopy techniques. Specifically, reductions in the formation of oxidation radicals, namely COOR and ester-carbonyl RCOOR bands were reduced.

Tensile test specimens were prepared using both beta carotene doped UHMWPE powder and pristine, undoped, UHMWPE powder. A comparison of the ultimate tensile stress (strength at break) revealed no statistical difference (P<0.24) between the beta carotene doped UHMWPE samples and the control undoped samples, using an unpaired t-test.

While in the foregoing, embodiments of the present invention have been set forth in considerable detail for the purposes of making a complete disclosure of the invention. Reference is made to the following examples to more specifically illustrate the present invention. However, the following examples is not deemed to limit the present invention in any manner.

EXAMPLE 1

350 mg of all-trans-beta-carotene was added (Sigma Chemical) added to 80 ml of isopropyl alcohol (2-propanol) at ambient temperature (≈20 degrees Celsius) then added 14 grams of ultra-high molecular-weight polyethylene (UHMWPE) powder. UHMWPE was 415 GUR grade 150 μm nominal diameter. The resulting solution strength was 4.375 mg/ml, beta-carotene-to-solvent. The UHMWPE powder was soaked for 6 hours, stirring periodically. The powder was then rinsed repeatedly with isopropyl alcohol until all visible beta carotene was removed. The UHMWPE powder was then air-dried at ambient conditions for 24 hours and stored in a sealed PE vial, in darkness.

Figure 1:
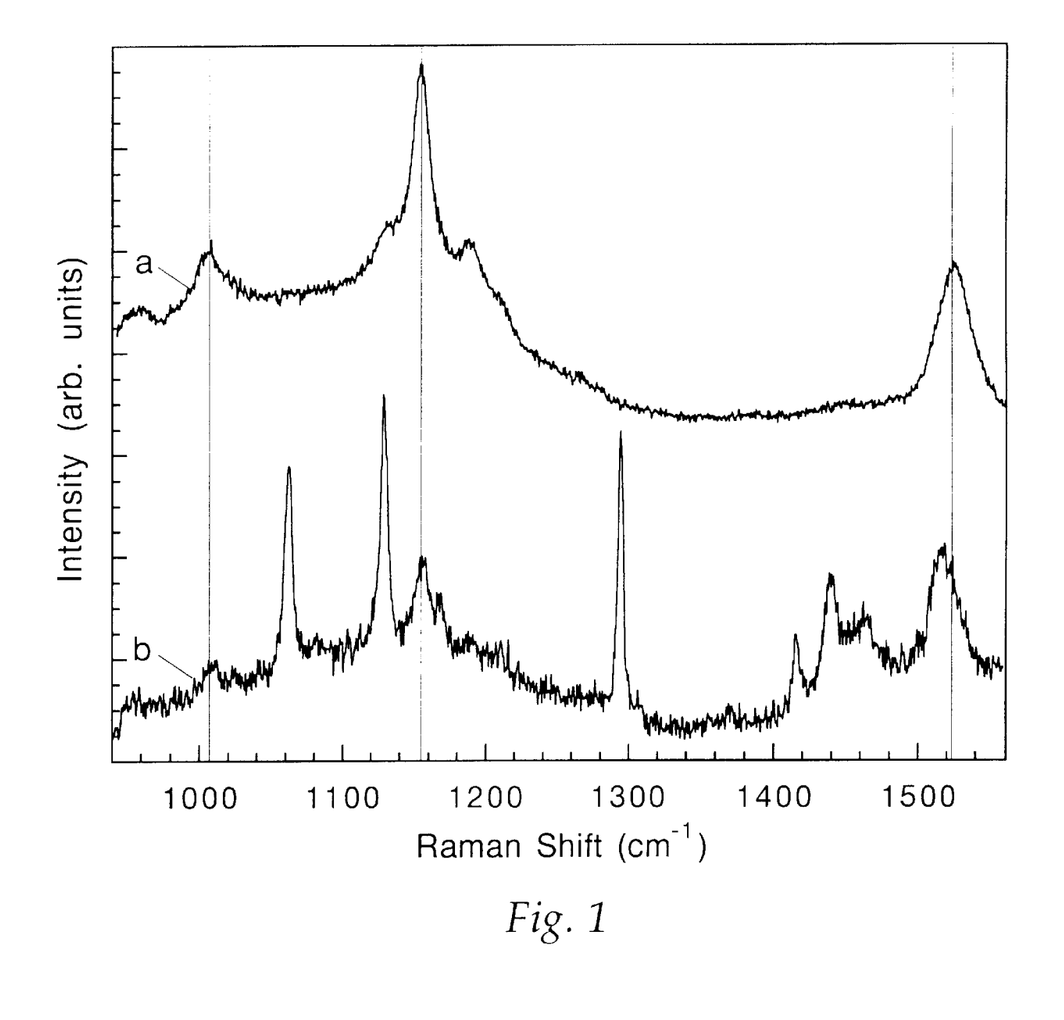
FIG. 1 is a graph depicting the Raman spectra of a beta carotene doped powder of Example 1.

FIG. 1 contains Raman spectra of the pure all-trans-beta-carotene reference sample, (a) and of the beta-carotene-doped UHMWPE powder (b). The Raman bands at 1005, 1155, and 1525 $cm^{-1}$ correspond to the primary beta-carotene peaks within the "fingerprint" region of UHMWPE. The shift of approximately 10 $cm^{-1}$ between the beta-carotene reference peak at 1525 $cm^{-1}$ and the beta-carotene-doped UHMWPE powder was due to changes in the conformation of the conjugated C=C double bonds of the beta-carotene backbone structure (Saito, et al., J. Raman Spect., V14, 299, 1983). This is evidence of some molecular interaction between the beta-carotene and UHMWPE.

Figure 2:
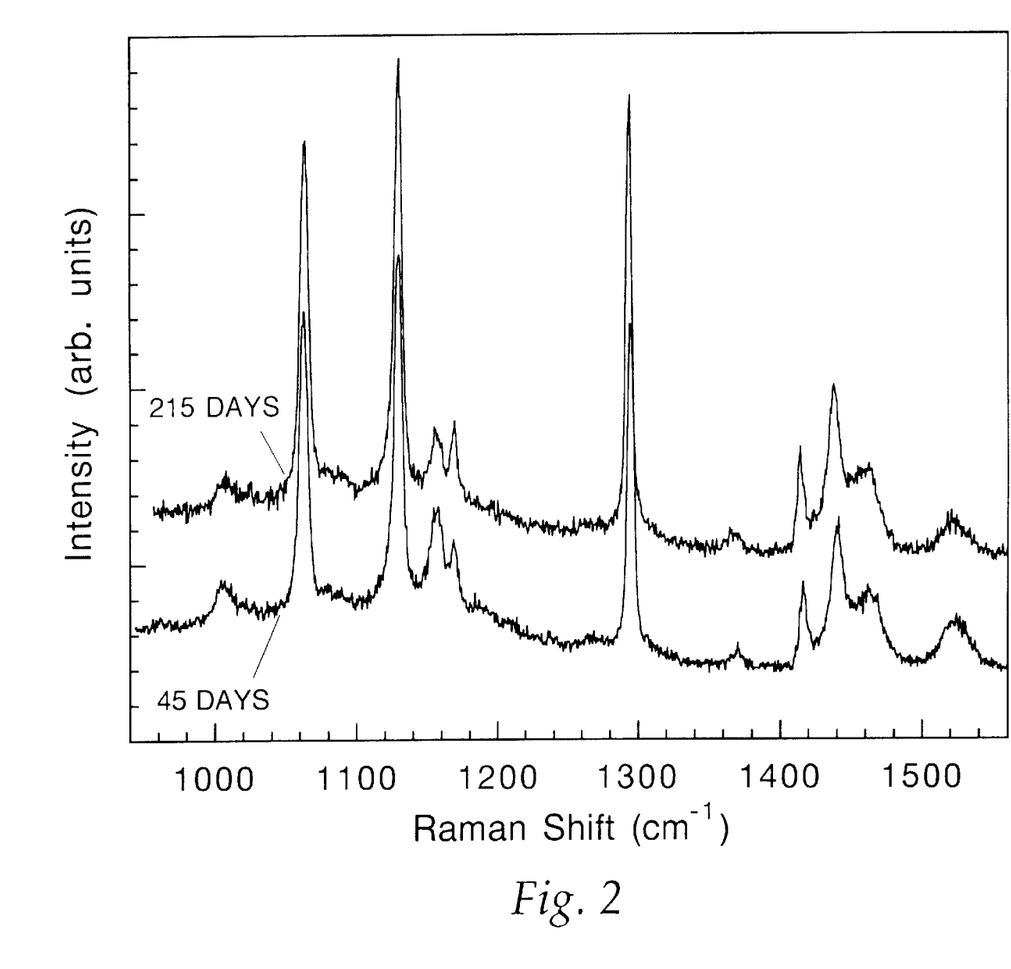
FIG. 2 is a graph depicting the Raman spectra of a beta carotene doped powder of Example 1 after a certain period of time.

FIG. 2 contains the Raman spectra of the same beta-carotene-doped UHMWPE powder (b) recorded at 45 and 215 days after doping. The beta-carotene-doped UHMWPE was stored in a sealed container with air, in darkness, and at ambient temperature (21 degrees celsius). The Raman bands at 1005, 1155, and 1525 $cm^{-1}$ corresponding to the primary beta-carotene peaks and the Raman spectra at the two times are comparable.

EXAMPLE 2

250 mg of all-trans-beta-carotene (Sigma Chemical) was added to 100 ml of isopropyl alcohol at ambient temperature (21 degrees celsius). This solution was then added to 800 mg of ultra-high molecular-weight polyethylene (UHMWPE) powder. UHMWPE was 415 GUR grade, <100 μm nominal diameter. The resulting solution strength was 1.25 mg/ml, beta-carotene-to-solvent. The UHMWPE powder was soaked for 21 hours, stirring periodically. The powder was then filtered out with 1 μm-sized polycarbonate filter and rinsed repeatedly with isopropyl alcohol until all visible beta-carotene was removed. The UHMWPE powder was then air-dried at ambient conditions for 12 hours and stored in a sealed PE vial, in darkness.

Figure 3:
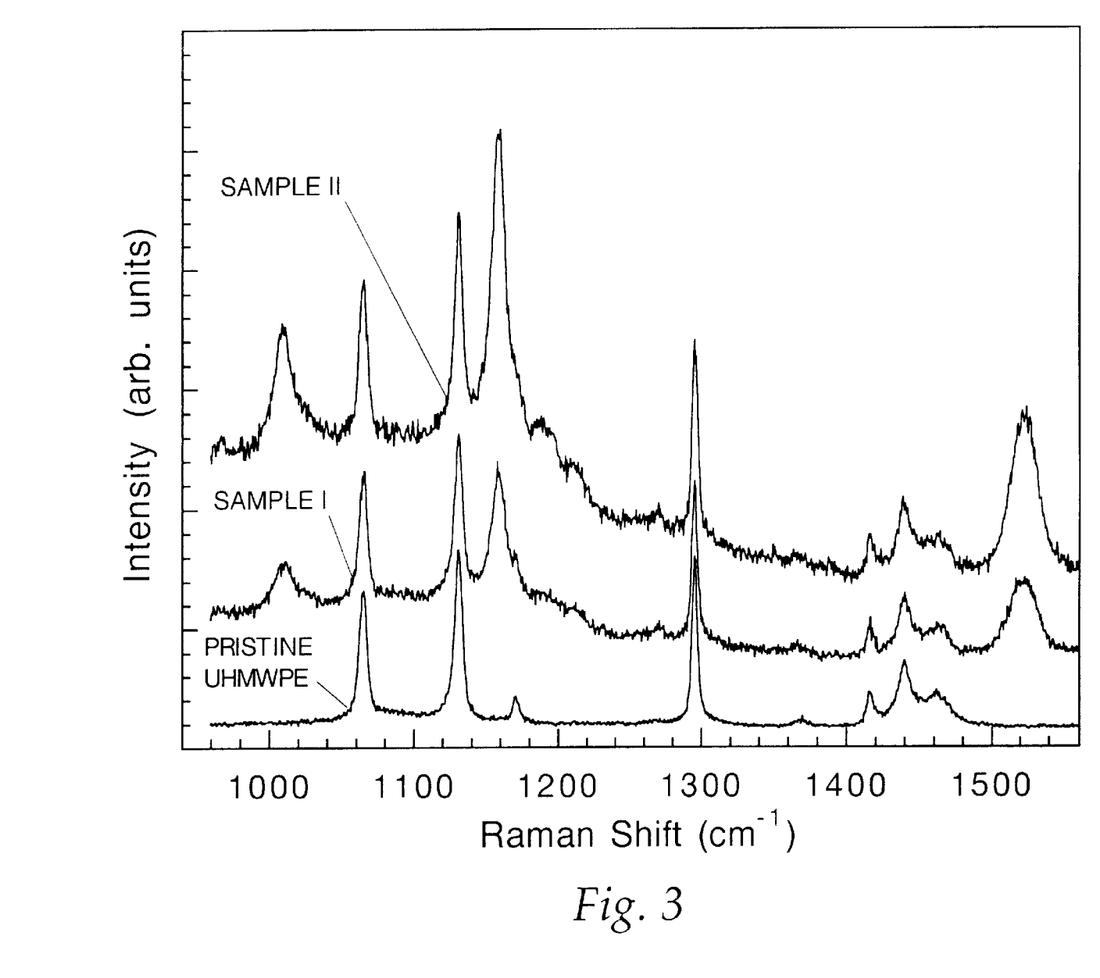
FIG. 3 is a graph depicting the Raman spectra of beta carotene doped powder of Example 2.

FIG. 3 contains the Raman spectra of two beta-carotene-doped UHMWPE powder samples recorded 18 days after doping and of pristine, UHMWPE reference powder (415 GUR). The Raman bands at 1005, 1155. and 1525 $cm^{-1}$ corresponding to the primary beta-carotene peaks are visible.

This example establishes the ability to dope UHMWPE powder with beta-carotene in isopropyl solutions of different concentrations and for different soaking times.

EXAMPLE 3

The UHMWPE powder and beta-carotene solution was prepared according to Example 2, except cyclohexane was substituted for isopropyl alcohol. The resulting solution strength was 1.25 mg/ml, beta-carotene-to-solvent (cyclohexane).

Figure 4:
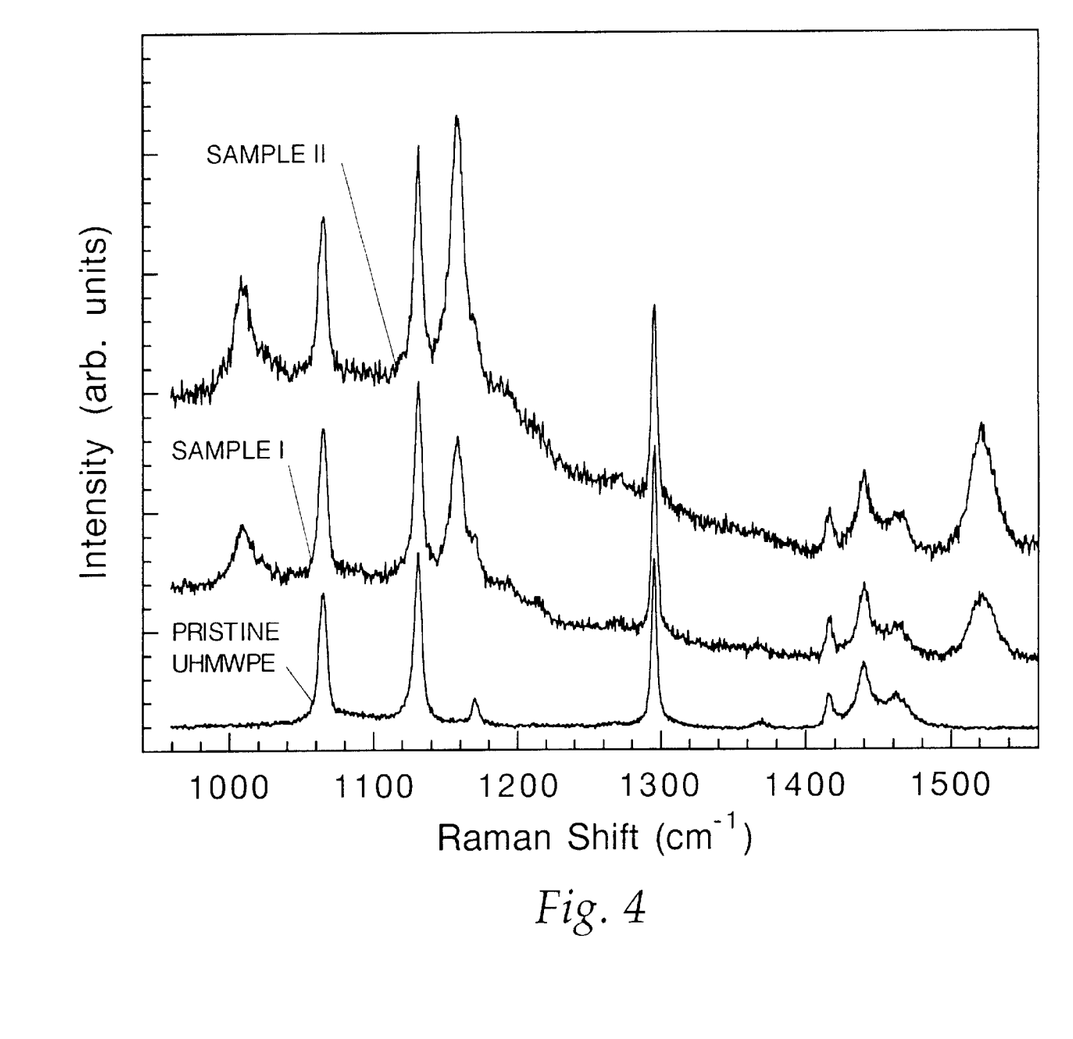
FIG. 4 is a graph depicting the Raman spectra of beta carotene doped powder of Example 3.

FIG. 4 contains the Raman spectra of two beta-carotene-doped UHMWPE powder samples recorded 18 days after doping, and of pristine, UHMWPE reference powder (415 GUR). The Raman bands at 1005, 1155, and 1525 $cm^{-1}$ corresponding to the primary beta-carotene peaks are visible.

This example establishes the ability to dope UHMWPE powder with beta-carotene in a cyclohexane solution and the ability to use alternative solvents for beta-carotene doping of UHMWPE.

EXAMPLE 4

Using the beta-carotene-doped UHMWPE powder of Example 1, bulk rods were molded as follows: A 3" deep by 0.25" diameter mold was filled with approximately 3 grams of beta-carotene-doped UHMWPE powder. The powder was compressed with a 0.25" piston to about 1,500 psi. The mold was then heated to 175 degrees celsius (±20° C.) for 45 minutes under a piston load of about 8 psi and atmospheric conditions. After 45 minutes, the molten beta-carotene-doped UHMWPE was compressed about 15 percent with the piston, and kept at a temperature of 175° C. for an additional 15 minutes under an 8 psi load. The mold was removed and cooled, with a resulting yield of several 2.75" long by 0.25" diameter solid samples. The beta-carotene-doped UHMWPE bulk samples were stored under atmospheric conditions in darkness.

Figure 5:
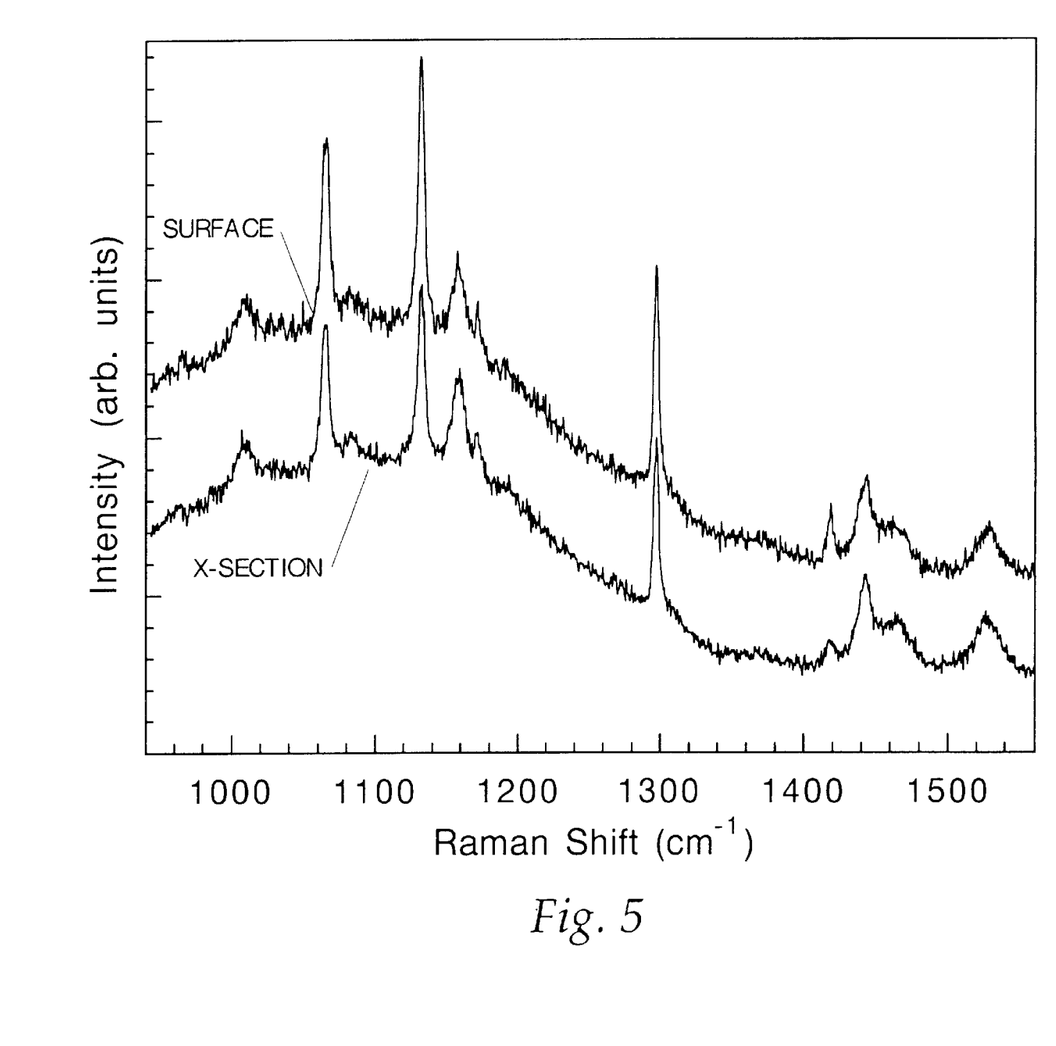
FIG. 5 is a graph depicting the Raman spectra of the surface and cross-sections of a beta carotene doped polymer of Example 4.

The molded samples were sectioned and Raman spectroscopy was performed on the surface and on internal cross-sections. FIG. 5 contains the Raman spectra of surface and a cross-section of the beta-carotene-doped UHMWPE bulk samples recorded 37 days after preparation. The Raman bands at 1005, 1155, and 1525 $cm^{-1}$ corresponding to the primary beta-carotene peaks, are visible both on the surface end on the internal cross-sections.

This example establishes the ability to mold beta-carotene-doped UHMWPE powder into solid, bulk beta-carotene-doped UHMWPE pieces, that exhibit a uniform distribution of beta-carotene throughout.

EXAMPLE 5

As depicted in Example 4, 2.75" by 0.25" diameter beta-carotene-doped UHMWPE sample specimens (test specimens) were prepared. In addition, samples were prepared in an identical manner with the exception of pristine GUR 415 powder (undoped) substituted for the beta-carotene-doped UHMWPE powder. Four beta-carotene-doped UHMWPE test specimens and four undoped test specimens were then machined (necked) in the center to a diameter of 0.185" (55% of cross-sectional area), yielding typical tensile-test specimens.

The eight tensile test specimens were then loaded under tension to failure in a tensile testing machine, and the ultimate tensile stress was calculated for each using the final measured diameter at the break. The ultimate tensile stresses for the four beta-carotene-doped tensile test specimens and the four undoped tensile test specimens are presented in Table 1.

TABLE 1

| Test Specimen | Ult. Tensile Stress (psi) |
|---|---|
| S1 undoped | 2450 |
| S2 undoped | 2497 |
| S3 undoped | 2427 |
| S4 undoped | 2912 |
| S5 doped | 1926 |
| S6 doped | 2865 |
| S7 doped | 1863 |
| S8 doped | 2225 |

The average and standard deviation of the four, undoped UHMWPE tensile test specimens was 2571 and 229 psi, respectively. The average and standard deviation of the four beta-carotene-doped UHMWPE test specimens was 2220 and 458 psi, respectively. This data was analyzed for statistical differences using an unpaired t-test. The t-value was 1.373, indicating no statistical difference between the ultimate tensile stress values of the undoped and beta-carotene-doped test specimens (p<0.24).

The example demonstrates the beta-carotene-doped UHMWPE powder may be used to mold bulk UHMWPE pieces that exhibit tensile strength comparable to similarly prepared, undoped UHMWPE pieces.

EXAMPLE 6

As in Example 4, solid beta-carotene-doped UHMWPE and undoped (control) UHMWPE sample specimens were prepared. The doped and undoped solid samples were analyzed using Fourier transform infrared (FTIR) spectroscopy in a surface reflectance mode.

The wavenumber region of interest corresponds to the oxidation radical bands between 1700 and 1780 $cm^{-1}$. The FTIR spectra presented in FIG. 6 correspond to the average of two beta-carotene-doped UHMWPE specimens, and to two undoped (control) UHMWPE specimens. The FTIR analysis was recorded 54 days after specimen molding, and the specimens were stored under atmospheric conditions, in darkness, prior to analysis.

Figure 6:
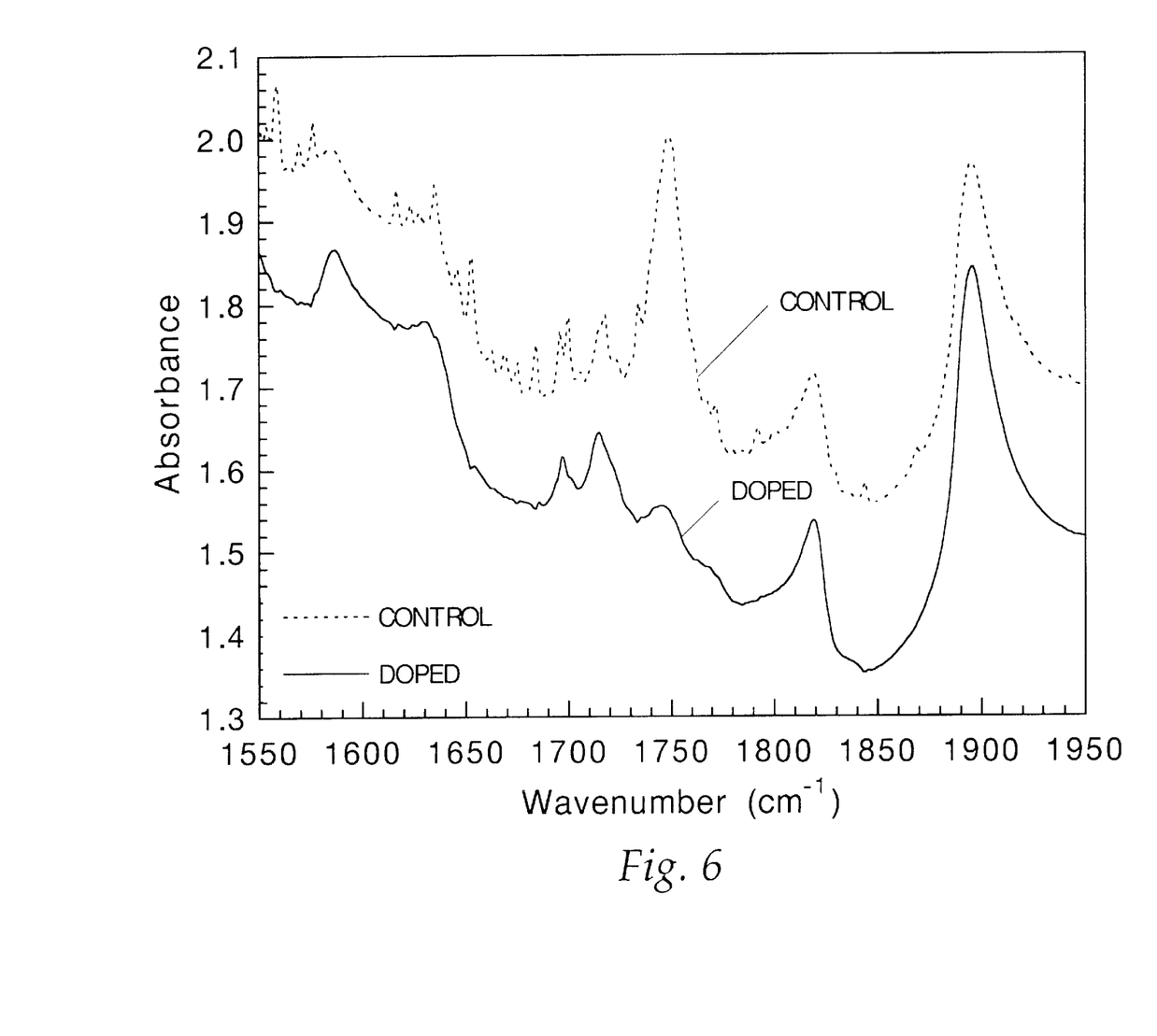
FIG. 6 is a graph depicting Fourier transform infrared (FTIR) spectra for samples prepared in Example 6.

The strong peak, near 1745 $cm^{-1}$, corresponding to an oxidation radical of the type COOR, was observed in the undoped (control) spectrum. This feature was not observed in the beta-carotene-doped UHMWPE sample spectrum.

This example establishes the utility of beta-carotene-doping in reducing the surface oxidation of beta-carotene-doped UHMPWE bulk samples.

EXAMPLE 7

As in Example 4, solid beta-carotene-doped UHMWPE and undoped UHMWPE sample specimens were prepared. The 0.25" diameter samples were sectioned along the major axis to expose the fresh, inner surface. The undoped and beta-carotene-doped UHMWPE samples were then soaked separately in a 3% $H_2O_2$ solution for 360 hours at ambient conditions. The $H_2O_2$ solution was replaced every 24 hours. The samples were then removed, rinsed in water, and then air-dried for 24 hours. The samples were then shelf-aged for 120 days under atmospheric conditions, in darkness.

Figure 7:
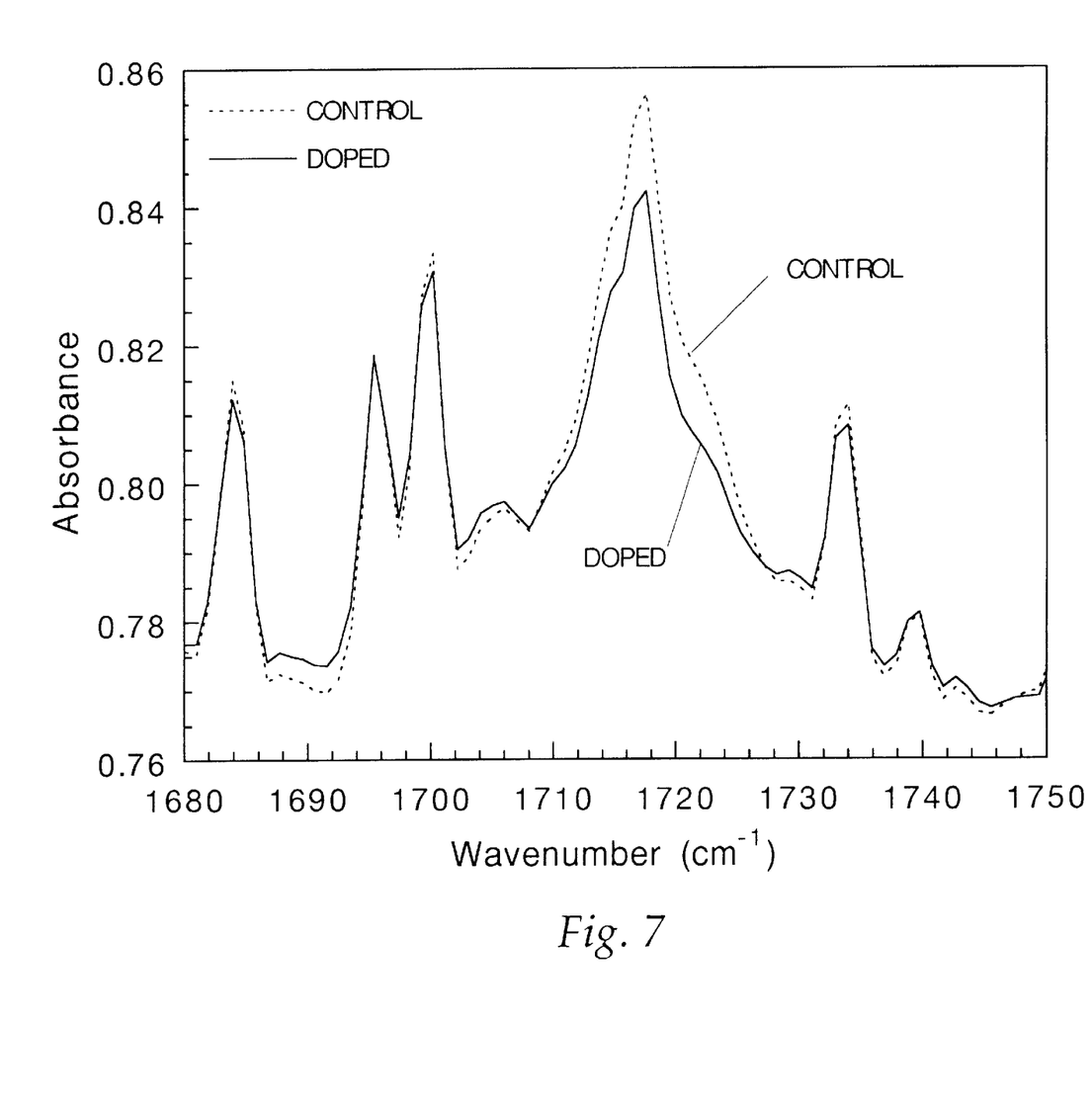
FIG. 7 is a graph of FTIR/spectroscopy of the samples prepared in Example 7.

The samples were analyzed with FTIR spectroscopy. Representative spectra for the beta-carotene-doped and undoped (control) UHMWPE samples are presented in FIG. 7. Sample oxidation was assessed using the 1717 $cm^{-1}$ band, corresponding to the ester-carbonyl oxidation radical RCOOR, as observed in FIG. 7. The oxidation was quantified by integrating the 1717 $cm^{-1}$ peak and normalizing by the non-oxidation absorbance baseline. The 1717 $cm^{-1}$ signal strengths are presented in Table 2 for the beta-carotene-doped and undoped (control) UHMWPE samples.

TABLE 2

| Oxidation Specimen | 1717 $cm^{-1}$ Signal |
|---|---|
| S1a undoped | 1.143 |
| S1b undoped | 1.167 |
| S2a undoped | 1.138 |
| S2b undoped | 1.137 |
| S3a doped | 1.133 |

TABLE 2-continued

| Oxidation Specimen | 1717 cm$^{-1}$ Signal |
|---|---|
| S3b doped | 1.128 |
| S4a doped | 1.118 |
| S4b doped | 1.119 |

The average and standard deviation of the four, undoped UHMWPE oxidation specimens was 1.146 and 0.0139, respectively. The average and standard deviation of the four beta-carotene-doped UHMWPE oxidation specimens was 1.125 and 0.0069, respectively. This data was analyzed for statistical differences using an unpaired t-test. The t-value was 2.811, showing a statistical difference between the 1717 cm$^{-1}$ signals of the undoped (control) and beta-carotene-doped oxidation specimens (p<0.03).

This example establishes the utility of beta-carotene-doping in reducing the ester-carbonyl oxidation (1717 cm$^{-1}$) of beta-carotene-doped UHMWPE bulk samples under weakly oxidative conditions.

EXAMPLE 8

Bulk pieces of commercial grade UHMWPE (1"×1"× 0.5") were soaked in three separate solution strengths of beta-carotene in cyclohexane, specifically 1.0 mg/ml, 0.5mg/ml, and 0.1 mg/ml beta-carotene-to-solvent (cyclohexane). The samples were soaked for 112 hours under ambient conditions, then rinsed repeatedly in isopropyl alcohol. The samples were then soaked in pure isopropyl for 2 hours, and air-dried for 6 hours. The samples were stored under atmospheric conditions, in darkness, prior to Raman analysis.

Figure 8:
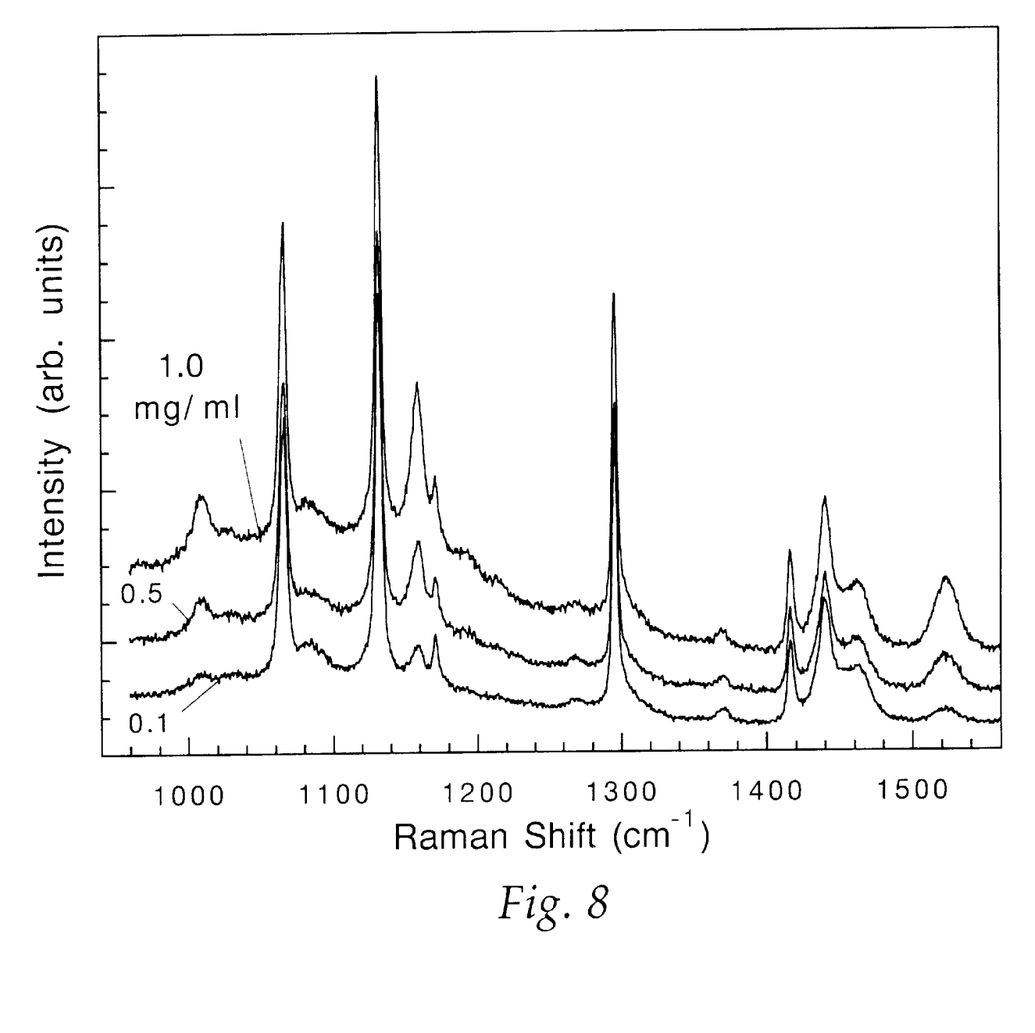
FIG. 8 is a graph depicting the Raman spectra for the samples presented in Example 8.

The Raman spectra of the beta-carotene-doped UHMWPE bulk samples are presented in FIG. 8 for the three doping concentrations 1.0, 0.5, and 0.1 mg/ml. The Raman bands at 1005, 1155, and 1525 cm$^{-1}$ corresponding to the primary beta-carotene peaks, are visible for all three doping concentrations. The beta-carotene signal was observed to decrease with decreasing beta-carotene solution strength, which is expected for a diffusion controlled process.

This example establishes the ability to control the doping of bulk UHMWPE material with beta-carotene in an appropriate beta-carotene-solvent solution by controlling time and beta-carotene-solvent solution strength.

EXAMPLE 9

Bulk pieces of commercial grade UHMWPE (1"×1"× 0.5") were soaked in a solution strength of 1.0 mg/ml of beta-carotene-to-cyclohexane, as a described in Example 8. Using a ⅛" precision end-mill, holes were bored into the surface of the beta-carotene-doped UHMWPE bulk samples to various depths (<400 μm).

Figure 9:
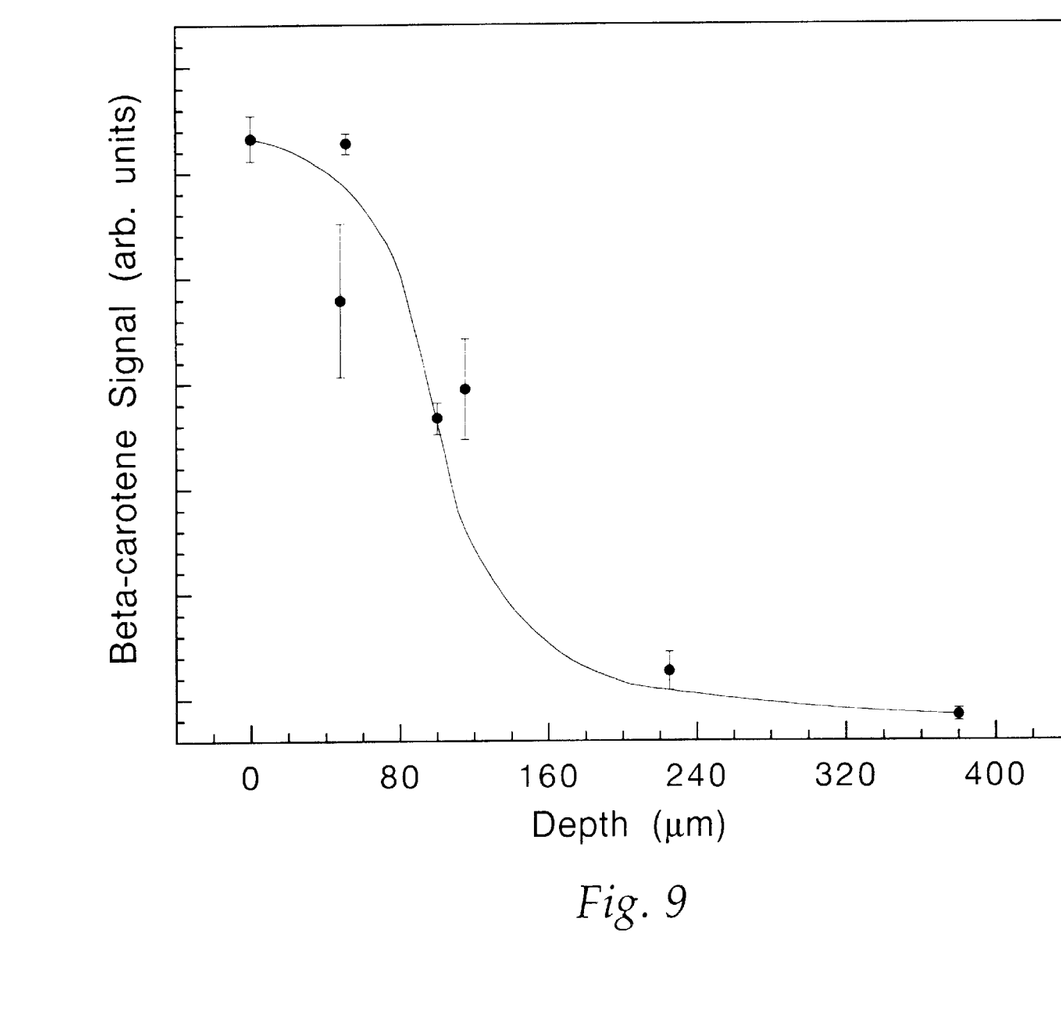
FIG. 9 is a graph depicting the existence of a beta carotene signal dependent on depth of the sample presented in Example 9.

Raman spectra were recorded at each depth below the surface, and the beta-carotene was analyzed. The amount of beta-carotene penetration was quantified using the 1525 cm$^{-1}$ beta-carotene Raman band. The 1525 cm$^{-1}$ peak was integrated and normalized by the non-beta-carotene signal baseline. The 1525 cm$^{-1}$ beta-carotene signal is presented in FIG. 9 as a function of depth below the surface. The beta-carotene penetrated to a depth of about 160 μm below the surface. The beta-carotene signal profile is characteristic of a diffusion controlled process.

This example establishes the ability control the doping of bulk UHMWPE material with beta-carotene in an appropriate beta-carotene-solvent solution, and to achieve penetration on the order of 100's μm below the sample surface.

EXAMPLE 10

Bulk pieces of commercial grade UHMWPE (1"×1"× 0.5") were soaked in a solution of xanthophyll ($C_{40}H_{56}O_2$), also known as lutein or alpha-carotene-3-3'-diol, in a corn oil base, specifically 75–80% xanthophyll (as purchased from ICN Biomedicals). The samples were soaked for 21 and 42 hours under ambient, conditions, then rinsed repeatedly in isopropyl alcohol. The samples were then soaked in pure isopropyl alcohol for 2 hours, and then air-dried for 6 hours. The samples were stored under atmospheric conditions, in darkness, prior to Raman analysis.

Figure 10:
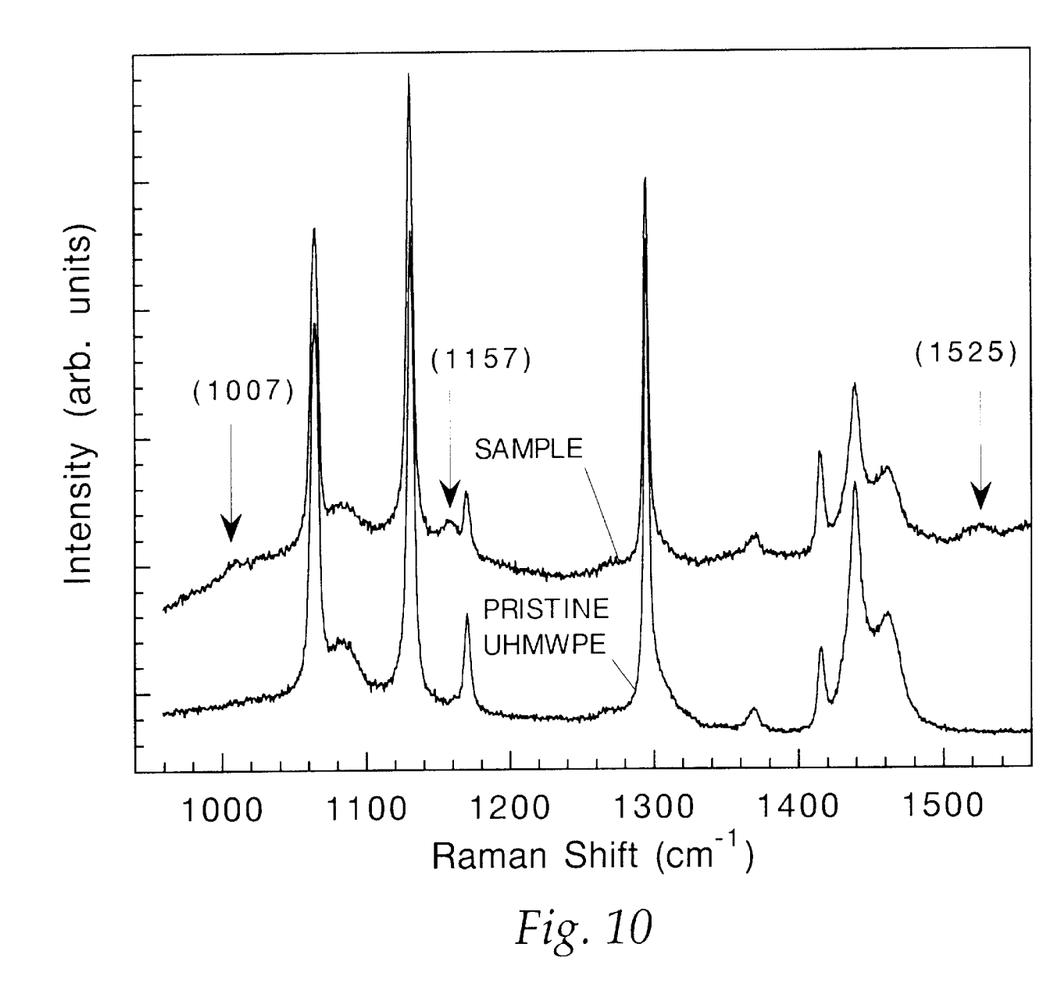
FIG. 10 is a graph representing a Raman study for the xanthophyll carotenoid employed in Example 10.

The Raman spectrum of the xanthophyll-doped UHMWPE bulk sample is presented in FIG. 10 for the sample soaked for 42 hours. The Raman bands at 1007, 1157, and 1525 cm$^{-1}$ corresponding to the primary xanthophyll peaks are visible. Also included in FIG. 10 is a reference spectrum for pristine UHMWPE. The xanthophyll signal was not observed on the UHMWPE sample soaked for 21 hours, apparently resulting from a decreased amount of absorbed xanthophyll which is a consistent with a diffusion controlled process.

This example establishes the ability to control the doping of bulk UHMWPE material with a beta-carotene-like carotenoid by doping time and an appropriate carotenoid solution.

What is claimed is:

1. A load bearing medical implant, consisting essentially of:
   a. a polymeric solid material; and
   b. a sufficient amount of a carotenoid compound doped into said polymeric solid material to produce a stable, oxidation resistant, matrix for forming the medical, load bearing implant.

2. The implant of claim 1 in which said polymer material is selected from the group consisting of polyethylene; high density polyethylene, ultra high molecular weight polyethylene.

3. The implant of claim 1 in which said carotenoid compound is present in a range of from trace amounts to 5% by weight.

4. The implant of claim 1 in which said carotenoid is beta carotene.

5. The implant of claim 1 in which said carotenoid is xanthophyll.

6. The composition of claim 1 in which said polymeric solid material is in a stock form.

7. A composition for the manufacture of a load bearing medical implant, consisting essentially of:
   a. a polymeric solid material in a powder form; and
   b. a sufficient amount of a carotenoid compound doped into said polymeric solid material to produce a stable, oxidation resistant, non-biodegradable matrix for forming a medical, load bearing implant.

* * * * *